United States Patent
Svatos (10) Patent No.: US 7,206,377 B2
(45) Date of Patent: Apr. 17, 2007

(54) PREDICTIVE ORGAN DYNAMICS DATABASE AND CODE

(75) Inventor: Michelle Marie Svatos, Oakland, CA (US)

(73) Assignee: Siemens Medical Solutions USA, Inc., Malvern, PA (US)

( * ) Notice: Subject to any disclaimer, the term of this patent is extended or adjusted under 35 U.S.C. 154(b) by 78 days.

(21) Appl. No.: 10/352,756

(22) Filed: Jan. 27, 2003

(65) Prior Publication Data

US 2004/0146141 A1 Jul. 29, 2004

(51) Int. Cl.
*A61N 5/10* (2006.01)
*G01N 23/04* (2006.01)

(52) U.S. Cl. .......................... 378/65; 378/62
(58) Field of Classification Search ............ 378/62–65; 600/439; 128/916
See application file for complete search history.

(56) References Cited

U.S. PATENT DOCUMENTS 6,325,758 B1 * 12/2001 Carol et al. ................ 600/439

2002/0150207 A1 * 10/2002 Kapatoes et al. ............. 378/65

OTHER PUBLICATIONS

*Webster's Unabridged Dictionary of the English Language*. 2nd ed. New York: Random House, Inc., 2001. (3 pgs total) Definition of "metric."
Liu, Xinming and Shaw, Chris, "a-Si: H/Csl (TI) flat-panel versus computed radiography for chest imaging applications: image quality metrics measurement" Medical Physics, 31, 98-110 (2004).
Multiscale Deformable Model Segmentation and Statistical Shape Analysis Using Medial Description, S. Joshi, S. Pizer, P. T. Flecture, P. Yushkevich, A. Thall, J.S. Marron, May 5, 2002, vol. 21, IEEE Transactions of Medical Imaging.

* cited by examiner

*Primary Examiner*—Edward J. Glick
*Assistant Examiner*—Irakli Kiknadze (57) ABSTRACT

A method of treating a region of interest with radiation by taking a three-dimensional image volume of a region of interest of a patient, defining the three-dimensional image volume, determining one or more metrics of the defined three-dimensional image volume and delivering a dose of radiation to the region of interest of a patient based on the one or more metrics.

41 Claims, 5 Drawing Sheets

PREDICTIVE ORGAN DYNAMICS DATABASE AND CODE

BACKGROUND OF THE INVENTION

1. Field of the Invention

The present invention relates generally to a radiation therapy devices and a method of radiation therapy, and more particularly, to radiation therapy devices and radiation therapy methods that use predictive organ dynamics data.

2. Discussion of Related Art

Conventional radiation therapy typically involves directing a radiation beam at a tumor in a patient to deliver a predetermined dose of therapeutic radiation to the tumor according to an established treatment plan. This is typically accomplished using a radiation therapy device such as the device described in U.S. Pat. No. 5,668,847 issued Sep. 16, 1997 to Hernandez, the contents of which are incorporated herein for all purposes.

The radiotherapy treatment of tumors involves three-dimensional treatment volumes which typically include segments of normal, healthy tissue and organs. Healthy tissue and organs are often in the treatment path of the radiation beam. This complicates treatment, because the healthy tissue and organs must be taken into account when delivering a dose of radiation to the tumor. While there is a need to minimize damage to healthy tissue and organs, there is an equally important need to ensure that the tumor receives an adequately high dose of radiation. Thus, the goal of radiation is to administer a treatment that has a high probability of tumor control while providing an acceptably low probability of complications in normal tissue.

With new image guided and adaptive radiotherapy techniques, a wealth of information about the patient geometry is obtained, and it is desirable to use this information to tailor the treatment for complication-free tumor control at every step in the treatment. This is difficult because the three-dimensional treatment volumes for the tumor typically also include normal organs. Thus healthy tissue and organs must be taken into account when delivering a dose of radiation to the tumor, and each type of tissue has a different type of response to varying degrees of radiation. While there is a need to minimize damage to healthy tissue and organs, there is an equally important need to choose a prescription in which the tumor receives an adequately high dose of radiation. Cure rates for many tumors are a sensitive function of the dose they receive, just as complication rates in normal organs are a function of the dose that they receive. Therefore, it is useful to have as much information as possible to understand how a certain type of tumor and certain normal structures have responded to radiation in other patients. It would be essential to monitor these quantities both during treatment during the follow up process.

Another factor that adds complexity to the planning process is the fact that many organs change size, shape and position from day to day. This also affects the prescription because margins must be added to these structures to account for the likely extent of the changes. A better understanding of the likely effect of these factors could result in a more accurate plan and higher probability of complication free tumor control.

Figure 1:
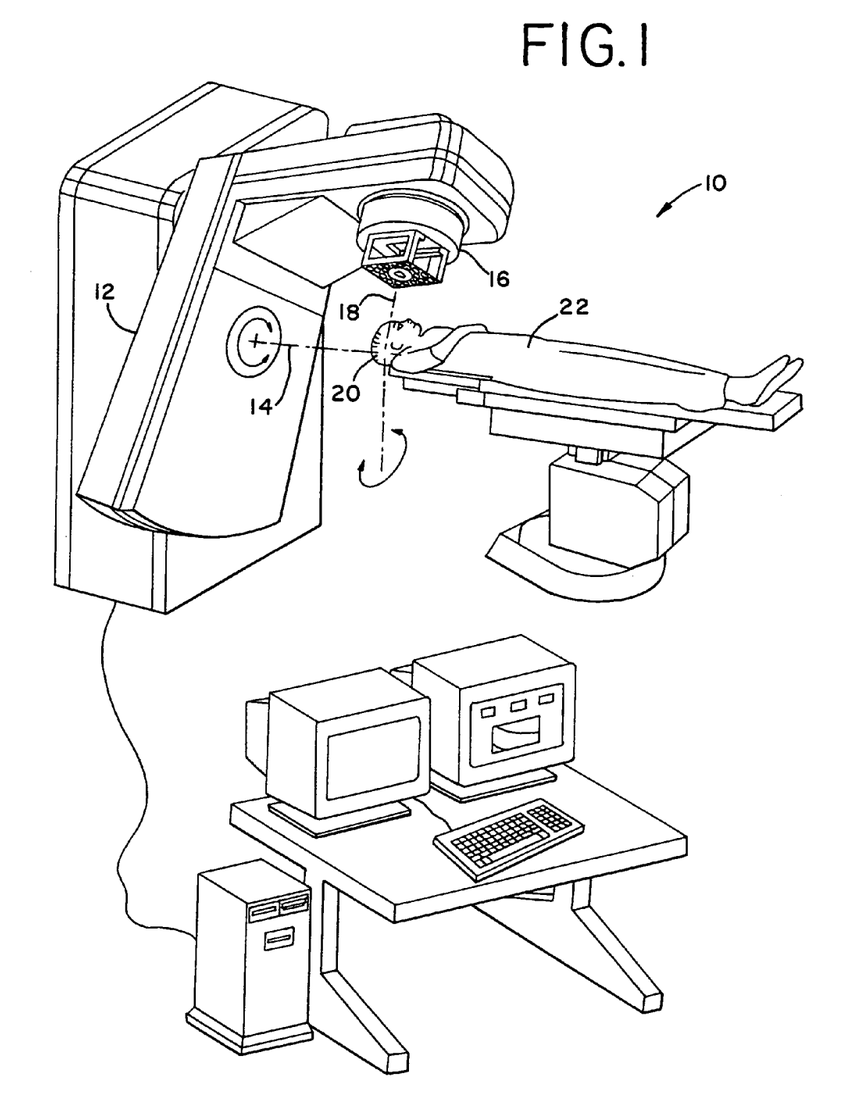
FIG. 1 shows an embodiment of a radiation therapy machine.

FIG. 1 schematically shows a radiation therapy machine 10 that includes a gantry 12 which can be swiveled around a horizontal axis of rotation 14 in the course of a therapeutic treatment. A treatment head 16 is fastened to a projection of the gantry 12. A linear accelerator (not shown) is located inside gantry 12 to generate the high energy radiation required for the therapy. The axis of the radiation bundle emitted from the linear accelerator and the gantry 12 is designated by beam path 18. Electron, photon or any other detectable radiation can be used for the therapy.

During a course of treatment, the radiation beam is trained on treatment zone 20 of an object 22, for example, a patient who is to be treated and whose tumor lies at the isocenter of the gantry rotation. Several beam shaping devices are used to shape radiation beams directed toward the treatment zone 20. For example, a multileaf photon collimator and a multileaf electron collimator can be arranged to shape the radiation beams. Each of these collimators may be separately controlled and positioned to shape beams directed at treatment zone 20.

Accordingly, it is an object of the present invention to tally informative statistics on the amount of dose required to treat specific types of tumors, and on the tolerance levels of specific normal tissues.

It is another object of the present invention to compile changes in the size and shape for each type of tissue and tumor and use the compiled changes with informative statistics to predict how organs will respond throughout the course of therapy.

SUMMARY OF THE INVENTION

One aspect of the present invention regards a method of treating an region of interest with radiation by identifying a region of interest of a patient. The method includes determining a treatment plan for the region of interest based on a statistical analysis between one or more metrics of the identified region of interest and a previously determined predictive dynamics database that includes information regarding the one or more metrics for corresponding regions of interest for a population of patients. Thereafter, a dose of radiation is delivered to the region of interest of a patient based on the determined treatment plan.

A second aspect of the present invention regards a radiation therapy device that includes a radiation source positioned to direct a beam of radiation along a beam path toward a region of interest of a patient and a treatment planning system connected to a control console, which is connected to the radiation source. The treatment planning system includes a memory that stores a predictive dynamics database that includes one or more metrics associated with the region of interest and probability distribution functions for the one or more metrics. The treatment planning system generates a treatment plan based on the stored predictive dynamics database and sends the treatment plan to the radiation source so as to control a dose of radiation generated by the beam of radiation at the region of interest.

A third aspect of the present invention regards a method of generating a predictive dynamics database used for treating a region of interest with radiation. The method includes taking a three-dimensional image volume of a region of interest of a patient, defining the three-dimensional image volume and determining one or more metrics of the defined three-dimensional image volume, forming probability distribution functions for each of the one or more metrics, and storing the one or more metrics and the formed probability distribution functions to form a predictive dynamics database.

Each aspect of the present invention increases the probability of tumor control and decreases the probability of complications in normal tissue.

Further characteristics and advantages of the present invention ensue from the following description of exemplary embodiments by the drawings.

DETAILED DESCRIPTION OF THE PREFERRED EMBODIMENTS

Figure 2:
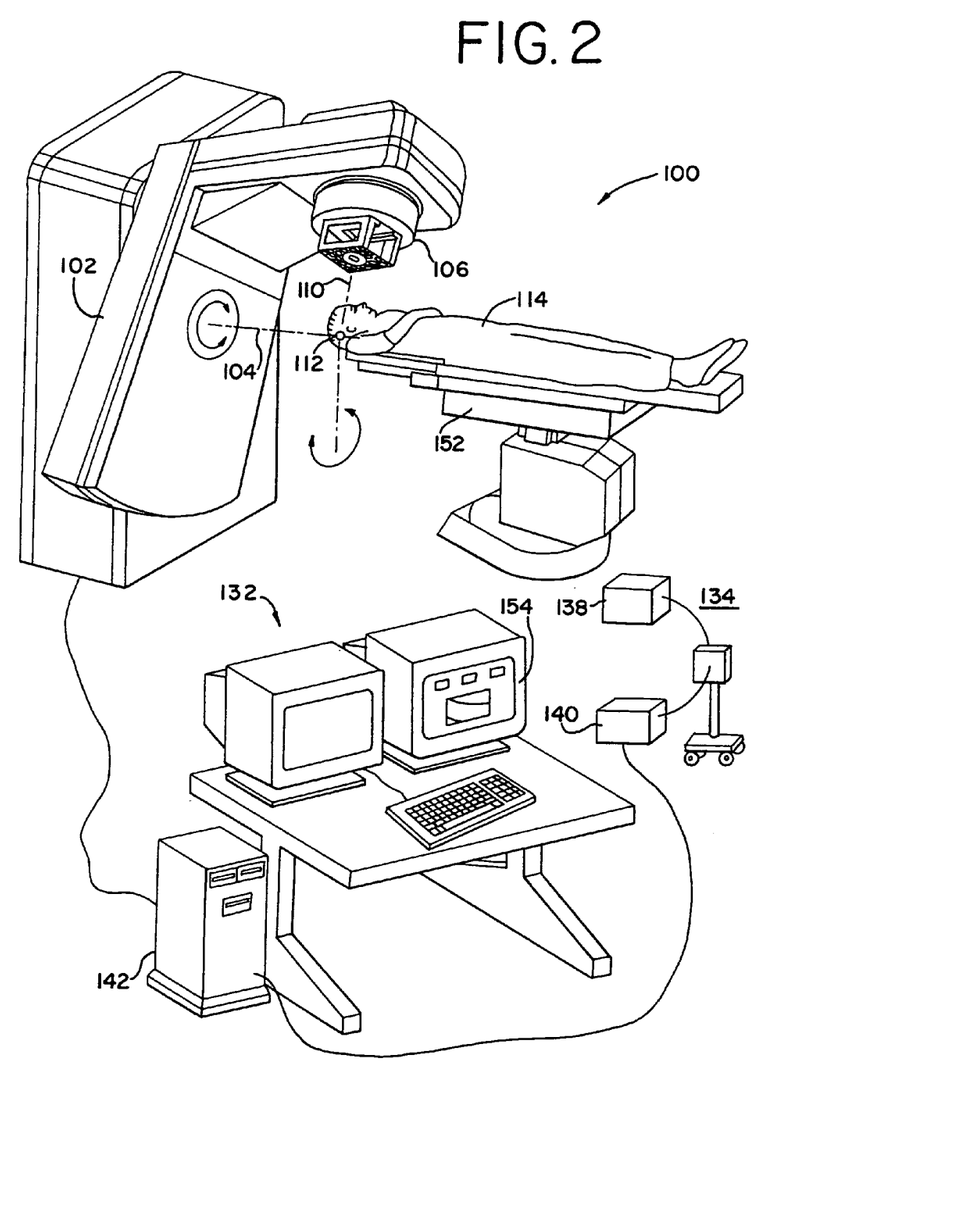
FIG. 2 shows an embodiment of a radiation therapy machine in accordance with the present invention.
Figure 3:
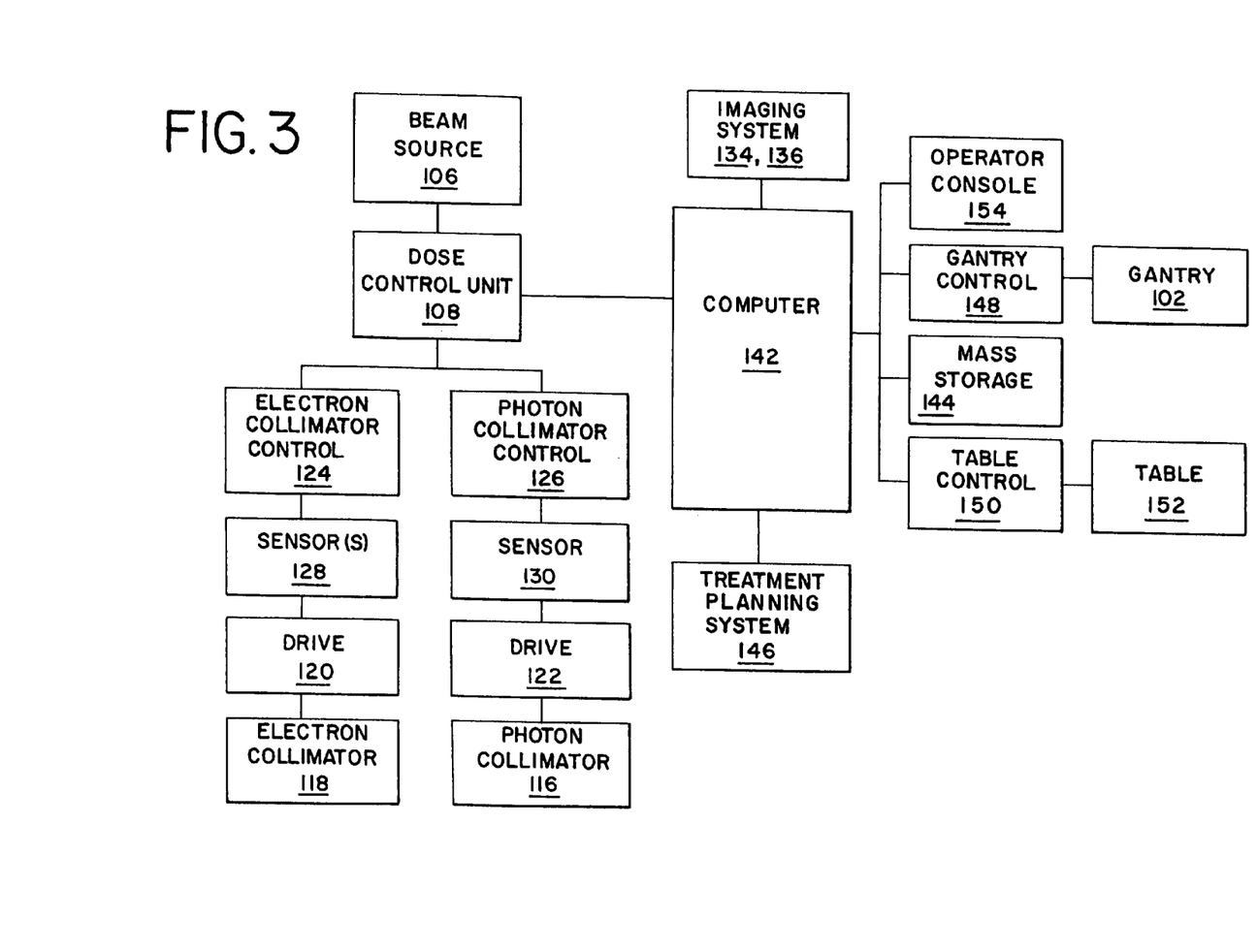
FIG. 3 shows a block diagram illustrating portions of the radiation therapy machine of FIG. 2.
Figure 4:
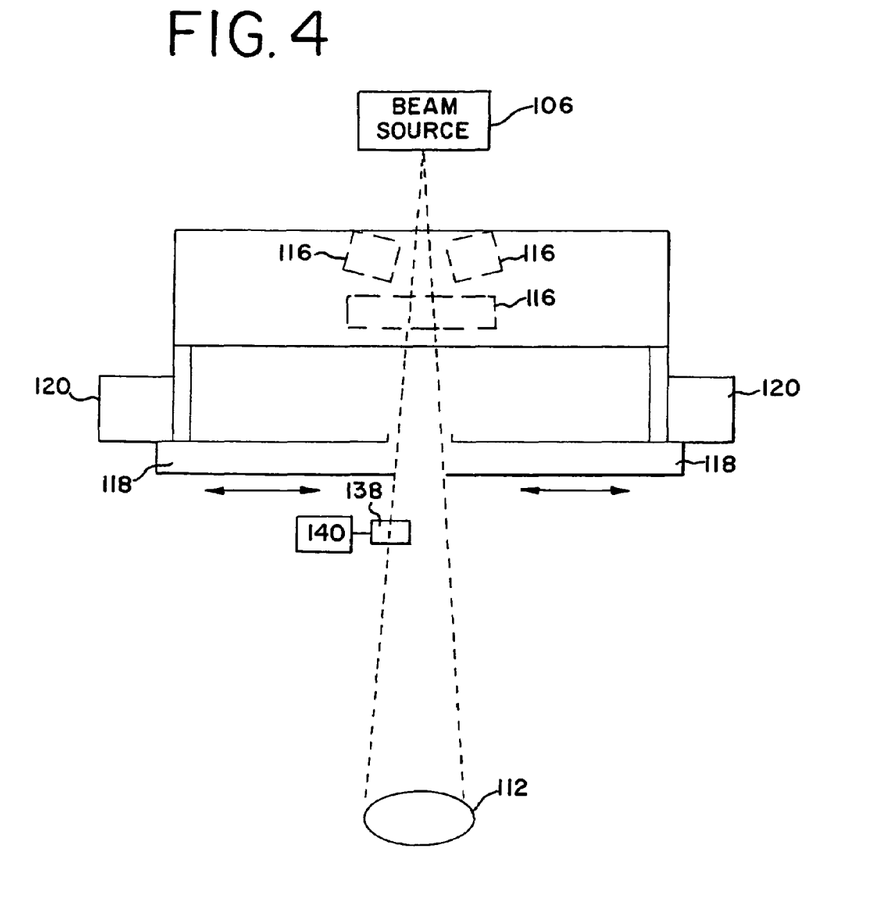
FIG. 4 schematically shows a collimator system to be used with the radiation therapy machine of FIG. 2.

A radiation therapy machine 100 that incorporates a number of the elements of the radiation therapy machine 10 of FIG. 1 is shown in FIGS. 2–4. The radiation therapy machine 100 includes a gantry 102 which can be swiveled around a horizontal axis of rotation 104 during the course of a therapeutic treatment. A beam source 106 is used to generate radiation beams in any of a number of ways well-known to those skilled in the art. For example, the beam source 106 may include a dose control unit 108 used to control a trigger system generating injector trigger signals fed to an electron gun in a linear accelerator (not shown) located inside the gantry 102 to produce the high energy radiation, such as an electron beam or photon beam, required for the therapy. The beam source 106 may include separate sources of radiation for photons and electrons. The axis of the radiation bundle emitted from the linear accelerator and the gantry 102 is designated by beam path 110.

During a course of treatment, the radiation beam is trained on treatment zone 112 of an object 114, for example, a patient who is to be treated and whose tumor lies at the isocenter of the gantry rotation. Several beam shaping devices are used to shape radiation beams directed toward the treatment zone 112. In particular, a multileaf photon collimator 116 and a multileaf electron collimator 118 are provided. Each of these collimators, as will be described further below, may be separately controlled and positioned to shape beams directed at the treatment zone 112.

The plates or leaves of the collimators 116 and 118 are made of a material, such as brass, tungsten or lead, substantially impervious to the emitted radiation. The collimator leaves or plates are mounted between the radiation source and the patient and positioned in order to delimit (conform) the field. Areas of the body, for example, healthy tissue, are therefore subject to as little radiation as possible and preferably to none at all.

Note that the plates or leaves of the collimators 116 and 118 are movable such that the distribution of radiation over the field need not be uniform (one region can be given a higher dose than another). In particular, the leaves of each collimator are individually driven by a drive unit 120, 122 and are positioned under the control of electron collimator control 124, photon collimator control 126 and sensor(s) 128 and 130. Drive units 120, 122 move the leaves of each collimator in and out of the treatment field to create a desired field shape for each type of beam. In one embodiment, where an electron beam is to be generated and primary electrons are to be used in a treatment, photon collimator control 126 operates to retract individual leaves of photon collimator 116, while electron collimator control 124 operates to position individual leaves of electron collimator 118 across the path of the electron beam to generate a desired electron field shape at the isocenter.

Note that while the radiation therapy machine 100 described above has the capability of providing either photon beam or electron beam treatments, the present invention is equally applicable to radiation therapy machines that have only one radiation source.

Figure 5:
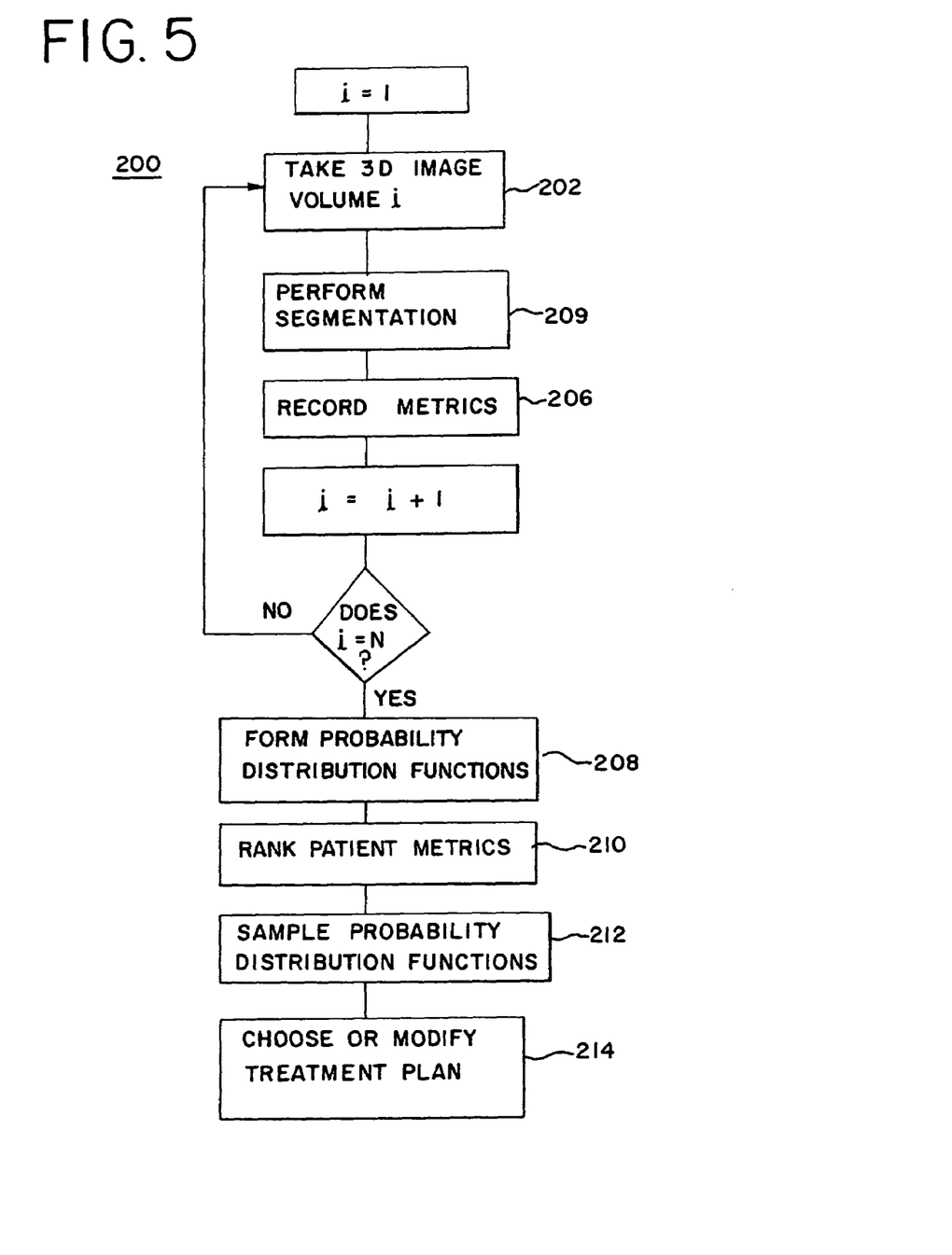
FIG. 5 shows a flow chart that shows a mode of a method of treating a region of interest with radiation in accordance with the present invention.

Radiation therapy machine 100 also includes a central treatment processing or control unit 132 that controls an adaptive radiation treatment process in accordance with the present invention. One mode of a possible adaptive radiation treatment process 200 is shown in FIG. 5. In this mode, a predictive organ dynamics database is established and updated per steps 202, 204, 206 and 208 to be described below. In particular, the predictive organ dynamics database includes information taken from N three-dimensional (3D) image volumes taken of a particular region of interest for a population of patients that may include a particular patient to be treated. The three-dimensional image volumes are taken in a well known manner, such as magnetic resonance imaging, CT or x-ray imaging, per step 202. The 3D image volume may be obtained at a different site or at the site of the radiation therapy machine 100 by an imaging system, such an x-ray imaging system 134 or a magnetic resonance imaging system 136. In the case of an x-ray imaging system, an imaging radiation source 138, such as an x-ray source, subjects the treatment zone 112 to radiation that is imaged by detector 140 in a well known manner. The image information is then fed from the detector 136 to a computer 142 of the central treatment planning unit 132.

Each time a 3D image volume of the patient is taken, the target for treatment and normal structures are defined in the 3D image volume in the central treatment planning or (virtual) simulation unit 132 by a known process called segmentation per step 204. It is important that each segmentation of the 3D image volume be done as consistently as possible, using automatic techniques if they are available. Note that the segmentation process preferably includes consistently naming and defining the organs shown in the 3D image volume so that they can be compared with other like named and defined organs of the patient and the entire patient population. Similarly, tumors and targets need to be adequately characterized or identified in the 3D image volume to ensure that they can be pooled or grouped with tumors and targets of similar type and stage of development.

After an image is appropriately segmented per step 204, a number of metrics, i.e., measurable quantities or qualities, are recorded based on the 3D image volume data sent to the central treatment processing unit 132 per step 206. For each organ, the position, size and shape and other organ parameters are determined and recorded. Examples of such organ parameters are:

1) The position of the organ—the x,y,z coordinates of the centroid of the organ of interest relative to other anatomical landmarks
2) The size of the organ—the volume of the organ of interest in cubic centimeters;
3) The shape of the organ—various metrics that quantify the shape of the organ of interest. Such metrics may include, but are not limited to, a symmetry index, number of inflection points, or ideally a variation of its generalized mid-line representation, such as defined in the article "Multi-scale Deformable Model Segmentation and Statistical Shape Analysis Using Medial Descriptions," by S. Joshi, S Pizer, P T Fletcher, P. Yushkevich, A Thall, and J S Marron, accepted for publication in: IEEE-Transaction on Medical Imaging, 2002;

4) The dose applied to the organ—the equivalent uniform dose (EUD) applied to the organ of interest at the time the 3D image volume is recorded; (could also be the average/mean dose with a standard deviation or homogeneity index; or other way of recording the dose)

5) The time of the image—the date and time of day the 3D image volume is recorded, and the amount of time elapsed since the therapy began;

6) The medical outcomes in the volume resulting from radiation—such as the grade of any complications for normal tissue or tumor response for the target at the time the 3D image volume is recorded;

7) The radiation sensitivity—the reaction a patient has to being treated with a particular type of radiation. Such a metric can be measured by performing a pre-treatment assay on skin or hair cells of the patient that can be used to rank where the patient falls with respect to the general patient population with regard to radiosensitivity. The metric will also be assessed throughout the course of therapy by the patient's physician; and 8) The identity of the patient—the identity of the patient associated with the 3D image volume. Such information may include a patient's past motion data to predict his future motion, for example. Also the age and sex of the patient would be important when seeking to apply the data to other patients who may be considered in the same class.

After the image is taken, segmented and its metrics are recorded per steps 202, 204, 206, the process is repeated as shown in FIG. 4. One 3D dataset may be obtained each day of treatment, or once a week during the approximately 6 weeks of therapy, and at each follow-up session after therapy is completed.

Once sufficient data entries have been made into each of these categories, probability distribution functions for each quantity as a function of dose and time are made in the central treatment processing unit 132 per step 208. Examples of probability distribution functions made in unit 132 are the probability of a tumor "kill" as a function of dose and the probability of a tumor "kill" as a function of time past therapy completion. Note that even if there is initially a correlation between dose and time (especially for the tumor), the distributions may eventually diverge during a follow up treatment, so it is important to categorize the data in both ways.

The metrics of step 206 and the probability distribution functions of step 208 are determined by the central treatment planning unit 132 and are stored in a mass storage memory 144 of the central treatment processing unit 132. The combination of one or more of the metrics of step 206 and probability distribution functions of step 208 are collectively deemed a predictive organ dynamics database. The predictive organ dynamics database includes metrics and probability distribution functions determined for images of other patients using the process 200 described above. In addition, the predictive organ dynamics database is not limited to a single region of interest but may include data regarding multiple regions of interest, such as different organs of a patient. The above described database functions in two ways: for intra-patient comparison and for inter-patient comparison that will be explained later. In radiation therapy, it is assumed that many quantities, such as organ motion and radiation response (on a cellular level) have a relatively narrow distribution intrinsic to the individual patient, and a wider distribution when these quantities are pooled over all similar patients.

Once a predictive organ dynamics database has been initially established based on data from a number of patients, the database can be applied to a patient during his or her treatment. At the beginning of the treatment there is typically little or no data on the individual patient stored in the database. In this case, a clinician may use expectation values from a larger patient population to prescribe a treatment for the patient. Accordingly, the initial treatments will be based on a treatment that would be effective for a majority of the population represented by the database. The initial treatment may be determined from the predictive organ dynamics database or by published clinical trials of similar patients.

After each of the initial treatments, a three-dimensional image volume of the region of interest of the patient is taken and added to the database per steps 202, 204, 206 and 208. Once the patient has undergone several treatment sessions, the database contains enough information that the treatment can be modified based on the previous data of the patient placed in the database. In this situation, the patient is positioned on table 152 for a therapy session. The identity of the patient is entered at the console 154 which results in the treatment planning system 146 performing a statistical analysis of one or more metrics of the previously accumulated data for the region of interest of the patient present in the database in conjunction with the probability distributions within the database. From that analysis, the patient is assigned a "rank" for each variable per step 210 and it is used to understand where the patient fits on the probability distribution function for each of the metrics determined in step 206. This rank predicts approximately the future status of one or more regions of interest of the patient, such as an organ, that is being treated by radiation. For example, if the patient after the first week of treatment shows that he has a widely varying prostate position compared to other patients in the first week of treatment (perhaps he's ranked in the 70–75% percentile), the clinician can sample the same probability distribution function at the same percentile or rank (70–75%) to predict what the motion of the prostate will be for subsequent treatments performed one or more days after the treatment. The prediction is for subsequent treatment days and the remainder of the course of therapy.

The above described predictive organ dynamics database may alone reveal interesting trends or may be further analyzed with deterministic methods or a Monte Carlo algorithm to sample all the probability distribution functions per step 210 and feed back their composite effect on planning to the treatment planning system 146, ultimately yielding a prediction of complication free survival probability for a given patient plan based on real patient data. The sampling of the probability distribution functions by the computer program can model the likely behavior of the organ or region of interest as a function of dose and time. The treatment planning system 146 is typically used to define and simulate a beam shape required to deliver an appropriate therapeutic dose of radiation to treatment zone 112. The sampling of each probability distribution function may be constrained to the narrow range indicated by the patient's rank for each variable.

This sampled information is used by the treatment planning system 146 of the central treatment processing or control unit 132 to influence the choice between various treatment plans or to modify a selected treatment plan applied to a particular patient's region of interest, such as an organ, per step 214 to optimize the outcome of the treatment. For example, if the sampled information shows that the organ being treated is likely to move a lot in the superior direction, the treatment planning system 146 will develop a treatment plan with a large margin in the superior direction.

As another example, if a sensitive structure in the field has a high probability that its physiology will fail even with a low dose, a plan that is very conservative with respect to the dose to that organ will be chosen, even at the expense of dosing other, less sensitive, organs or perhaps even at the expense of dosing the tumor. Note that the treatment plan determined by step 214 includes controlling the radiation strength, duration and shape as well as the position of the radiation source and the patient. For example, a patient is placed in proper position by having the computer 144 send signals to a gantry control 148, and a table control 150 that controls table 152.

After the patient is properly positioned the electron radiation beam is applied to the treatment region to generate a desired dosage. The computer 144 is also operatively coupled to the dose control unit 108 which includes a dosimetry controller and which is designed to control the beam source 106 to generate a desired beam achieving desired isodose curves. After a treatment plan is implemented, the predictive organ dynamics database is updated by imaging the region of interest during a patient follow up phase and entering metric data via the process 200 explained previously.

As the predictive organ dynamics database is enlarged by the number of patients entered and the time spans from which particular regions of interest are enlarged, the sampled information ultimately can be used to predict future complications and survival rates for a particular patient's treatment plan based on other patient data.

Those skilled in the art will appreciate that various adaptations and modifications of the just described preferred embodiments can be configured without departing from the scope and spirit of the invention. Therefore, it is to be understood that, within the scope of the appended claims, the invention may be practiced other than as specifically described herein.

The invention claimed is:

1. A method of treating a region of interest with radiation, the method comprising:
   identifying a region of interest of a patient to be treated with radiation;
   determining a treatment plan for said region of interest based on a statistical analysis between one or more metrics of said identified region of interest and a previously determined predictive dynamics database that includes information regarding said one or more metrics for corresponding regions of interest for a population of patients;
   delivering a dose of radiation to said region of interest of said patient based on said determined treatment plan.

2. The method of claim 1, wherein said information is determined from three-dimensional image volumes obtained from said population of patients.

3. The method of claim 1, wherein said region of interest is an organ of said patient.

4. The method of claim 1, wherein said one or more metrics comprises a position of said region of interest.

5. The method of claim 1, wherein said one or more metrics comprises a shape of said region of interest.

6. The method of claim 1, wherein said one or more metrics comprises a size of said region of interest.

7. The method of claim 1, wherein said one or more metrics comprises a dose applied to said region of interest.

8. The method of claim 1, wherein said one or more metrics comprises a grade open area of said three dimensional image volume.

9. The method of claim 1, wherein said one or more metrics comprises a radiation response.

10. The method of claim 1, wherein said information includes a probability distribution function for each one of said one or more metrics.

11. The method of claim 10, wherein said delivering said radiation dose is based on said formed probability distribution functions.

12. The method of claim 10, further comprising assigning to said patient a rank for said probability distributions for each one of said one or more metrics.

13. The method of claim 12, further comprising predicting a future status of said region of interest based on said assigning.

14. The method of claim 10, further comprising sampling said probability distribution functions.

15. The method of claim 14, further comprising predicting a probability of survival using a particular treatment plan on said region of interest based on said probability distribution functions.

16. The method of claim 14, further comprising predicting a probability of complication free survival using a particular treatment plan on said region of interest based on said sampled probability distribution functions.

17. The method of claim 10, further comprising predicting a probability of survival using a particular treatment plan on said region of interest based on said probability distribution functions.

18. The method of claim 10, further comprising predicting a probability of complication free survival using a particular treatment plan on said region of interest based on said sampled probability distribution functions.

19. The method of claim 10, wherein said determining is based on choosing a particular treatment plan for said region of interest based on said probability distribution functions.

20. The method of claim 10, wherein said determining is based on altering a particular treatment plan for said region of interest based on said probability distribution functions.

21. The method of claim 1 further comprising: taking a three-dimensional image volume of said region of interest of said patient; defining said three dimensional image volume; determining one or more metrics of said defined three dimensional image volume; and updating said previously determined predictive dynamics database with said determined one or more metrics.

22. A radiation therapy device, comprising:
   a radiation source positioned to direct a beam of radiation along a beam path toward a region of interest of a patient;
   a treatment planning system connected to said radiation source, said treatment planning system comprising a memory that stores a predictive dynamics database that includes one or more metrics associated with said region of interest and probability distribution functions for said one or more metrics, said treatment planning system generating a treatment plan based on said stored predictive dynamics database and sending said treatment plan to said radiation source so as to control a dose of radiation generated by said beam of radiation at said region of interest.

23. The radiation therapy device of claim 22, further comprising a collimator positioned between said radiation source and said region of interest, wherein a signal is sent from said treatment planning system to said collimator so as to control the position of said collimator and a shape of said beam of radiation.

24. The radiation therapy device of claim 22, wherein said radiation source comprises an electron radiation source.

25. The radiation therapy device of claim 22, wherein said radiation source comprises a photon radiation source.

26. The radiation therapy device of claim 22, further comprising an imaging device that generates an image of said region of interest subsequent to said beam of radiation being generated by said radiation source, said image is directed to said treatment planning system to update said predictive dynamics database.

27. The radiation therapy device of claim 26, wherein said imaging device is an x-ray imaging system.

28. The radiation therapy device of claim 26, wherein said imaging device is a magnetic resonance imaging system.

29. A method of generating a predictive dynamics database used for treating a region of interest with radiation, the method comprising:
   taking a three-dimensional image volume of a region of interest of a patient;
   defining said three-dimensional image volume; determining one or more metrics of said defined three-dimensional image volume;
   forming probability distribution functions for each of said one or more metrics; and
   storing said one or more metrics and said formed probability distribution functions to form a predictive dynamics database.

30. The method of claim 29, further comprising:
   determining a further set of one or more metrics; and
   updating said predictive dynamics database with said further set of one or more metrics.

31. The method of claim 29, wherein said taking comprises taking a magnetic resonance image of said region of interest.

32. The method of claim 29. Wherein said taking comprises taking a CT image of said region of interest.

33. The method of claim 29, wherein said defining comprises segmentation.

34. The method of claim 33, wherein said defining comprises establishing a name for said region of interest.

35. The method of claim 29, wherein said region of interest is an organ of said patient.

36. The method of claim 29, wherein said one or more metrics comprises a position of said region of interest.

37. The method of claim 29, wherein said one or more metrics comprises a shape of said region of interest.

38. The method of claim 29, wherein said one or more metrics comprises a size of said region of interest.

39. The method of claim 29, wherein said one or more metrics comprises a dose applied to said region of interest.

40. The method of claim 29, wherein said one or more metrics comprises a grade of an area of said three dimensional image volume.

41. The method of claim 29, wherein said one or more metrics comprises a radiation response.

* * * * *